United States Patent
Borglin et al.

(10) Patent No.: US 10,856,965 B2
(45) Date of Patent: Dec. 8, 2020

(54) GRAFT MATERIAL HAVING HEATED PUNCTURE STRUCTURE AND METHOD

(71) Applicant: Medtronic Vascular, Inc., Santa Rosa, CA (US)

(72) Inventors: Zachary Borglin, San Francisco, CA (US); Keith Perkins, Santa Rosa, CA (US); Darren Galligan, San Francisco, CA (US); Julie Benton, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 156 days.

(21) Appl. No.: 16/143,932

(22) Filed: Sep. 27, 2018

(65) Prior Publication Data

US 2019/0159883 A1    May 30, 2019

Related U.S. Application Data

(60) Provisional application No. 62/591,601, filed on Nov. 28, 2017.

(51) Int. Cl.
*A61F 2/06* (2013.01)
*D04H 1/485* (2012.01)
(Continued)

(52) U.S. Cl.
CPC .............. *A61F 2/07* (2013.01); *A61F 2/0077* (2013.01); *A61F 2/06* (2013.01); *A61L 27/18* (2013.01);
(Continued)

(58) Field of Classification Search
CPC ........ A61F 2/06; A61F 2/07–2002/077; A61F 2210/0071; A61F 2240/00;
(Continued)

(56) References Cited

U.S. PATENT DOCUMENTS

| 4,469,734 A * | 9/1984 | Minto ................... D04H 1/425 |
| | | 156/148 |
| 5,769,884 A * | 6/1998 | Solovay ................... A61F 2/07 |
| | | 606/194 |

(Continued)

FOREIGN PATENT DOCUMENTS

| DE | 102014110013 A1 * | 1/2016 | ............... A61F 2/07 |
| EP | 0144534 A2 | 6/1985 | |

(Continued)

OTHER PUBLICATIONS

Machine translation of German patent DE102014110013A1 published Jan. 2016. (Year: 2016).*

(Continued)

*Primary Examiner* — Paul B Prebilic

(57) ABSTRACT

A needle lattice is used to form openings within a graft material to selectively enhance permeability of a prosthesis for tissue integration therein. The needle lattice may be disposed on, for example, a surface of a roller or press. The needle lattice precisely places openings in any pattern and location, and on any textile that forms the graft material. The needle lattice can be heated to fuse the surrounding material of the openings of the textile to prevent movement of the textiles and to prevent collapse of the openings. All parameters of the openings, including varying density, patterns, and size of each opening, can be controlled, allowing for the opportunity to selectively enhance and optimize the permeability of the graft material in a vessel. The needle lattice can quickly form multiple openings within a graft material, allowing for quick manufacturing of the prosthesis.

9 Claims, 15 Drawing Sheets

(51) Int. Cl.

| | |
|---|---|
| *A61F 2/07* | (2013.01) |
| *D02G 3/36* | (2006.01) |
| *A61L 27/58* | (2006.01) |
| *D03D 1/00* | (2006.01) |
| *D03D 15/00* | (2006.01) |
| *D02G 3/44* | (2006.01) |
| *A61F 2/00* | (2006.01) |
| *A61L 27/18* | (2006.01) |
| *A61L 27/54* | (2006.01) |
| *A61L 27/56* | (2006.01) |
| *A61L 31/14* | (2006.01) |
| *A61L 31/16* | (2006.01) |
| *A61L 31/02* | (2006.01) |
| *A61L 31/06* | (2006.01) |
| *A61L 31/10* | (2006.01) |
| *B23K 26/388* | (2014.01) |
| *A61L 31/04* | (2006.01) |

(52) U.S. Cl.
CPC .............. *A61L 27/54* (2013.01); *A61L 27/56* (2013.01); *A61L 27/58* (2013.01); *A61L 31/022* (2013.01); *A61L 31/06* (2013.01); *A61L 31/10* (2013.01); *A61L 31/148* (2013.01); *A61L 31/16* (2013.01); *D02G 3/36* (2013.01); *D02G 3/448* (2013.01); *D03D 1/00* (2013.01); *D03D 15/0027* (2013.01); *D03D 15/0094* (2013.01); *A61F 2002/0081* (2013.01); *A61F 2002/065* (2013.01); *A61F 2002/075* (2013.01); *A61F 2002/077* (2013.01); *A61F 2210/0004* (2013.01); *A61F 2210/0014* (2013.01); *A61F 2210/0057* (2013.01); *A61F 2210/0071* (2013.01); *A61F 2210/0076* (2013.01); *A61F 2220/0075* (2013.01); *A61F 2230/0069* (2013.01); *A61F 2240/001* (2013.01); *A61F 2250/0003* (2013.01); *A61F 2250/003* (2013.01); *A61F 2250/0023* (2013.01); *A61F 2250/0024* (2013.01); *A61F 2250/0031* (2013.01); *A61F 2250/0051* (2013.01); *A61F 2250/0067* (2013.01); *A61F 2250/0068* (2013.01); *A61F 2250/0069* (2013.01); *A61F 2250/0076* (2013.01); *A61L 31/043* (2013.01); *A61L 2300/258* (2013.01); *A61L 2300/404* (2013.01); *A61L 2300/41* (2013.01); *A61L 2300/412* (2013.01); *A61L 2300/42* (2013.01); *A61L 2420/02* (2013.01); *A61L 2420/08* (2013.01); *B23K 26/388* (2013.01); *D10B 2101/20* (2013.01); *D10B 2331/04* (2013.01); *D10B 2509/06* (2013.01)

(58) Field of Classification Search
CPC ........ A61F 2240/001; A61F 2250/0023; A61F 2250/0024; A61F 2250/0051; A61F 2250/0068; A61F 2250/0069; D04H 1/485; D04H 1/46
See application file for complete search history.

(56) References Cited

U.S. PATENT DOCUMENTS

| | | | |
|---|---|---|---|
| 6,278,079 B1* | 8/2001 | McIntyre | A61F 2/07 |
| | | | 219/121.67 |
| 8,241,543 B2* | 8/2012 | O'Donnell | A61F 13/5122 |
| | | | 264/154 |
| 9,486,346 B2 | 11/2016 | Argentine | |
| 2005/0027270 A1* | 2/2005 | Cree | B32B 5/022 |
| | | | 604/383 |
| 2005/0220848 A1 | 10/2005 | Bates | |
| 2007/0282160 A1 | 12/2007 | Sheu et al. | |
| 2008/0188923 A1 | 8/2008 | Chu | |
| 2009/0043330 A1 | 2/2009 | To | |
| 2013/0267137 A1 | 10/2013 | Peniston et al. | |
| 2017/0231749 A1 | 8/2017 | Perkins et al. | |
| 2017/0360993 A1 | 12/2017 | Argentine et al. | |
| 2018/0193175 A1* | 7/2018 | Bluecher | A61F 2/848 |

FOREIGN PATENT DOCUMENTS

| | | |
|---|---|---|
| EP | 0397500 B1 | 2/1995 |
| EP | 1820889 B1 | 3/2009 |
| WO | 2000047135 A1 | 8/2000 |
| WO | 2004037116 A2 | 5/2004 |
| WO | 2011103141 A1 | 8/2011 |
| WO | 2013097841 A1 | 7/2013 |
| WO | 2013128718 A1 | 9/2013 |
| WO | 2014133798 A1 | 9/2014 |
| WO | 2017079659 A1 | 11/2016 |

OTHER PUBLICATIONS

PCT/US2018/062482, The International Search Report and the Written Opinion of the Int'l Searching Authority, dated Mar. 27, 2019, 14 pages.
PCT/US2018/062512, The International Search Report and the Written Opinion of the Int'l Searching Authority, dated Apr. 17, 2019, 12 pages.
PCT/US2018/062516, The International Search Report and the Written Opinion of the Int'l Searching Authority, dated Mar. 27, 2019, 13 pages.
PCT/US2018/062549, The International Search Report and the Written Opinion of the Int'l Searching Authority, dated Mar. 28, 2019, 13 pages.
PCT/US2018/062581, The International Search Report and the Written Opinion of the Int'l Searching Authority, dated Mar. 27, 2019, 15 pages.
PCT/US2018/062589, The International Search Report and the Written Opinion of the Int'l Searching Authority, dated Mar. 27, 2019, 13 pages.
U.S. Appl. No. 62/591,601, titled "Advanced Graft Materials for Endovascular Applications", filed Nov. 28, 2017.
U.S. Appl. No. 15/950,612, titled "Graft Materail Having Selectively Advanced Permeability Structure and Method", filed Apr. 11, 2018.
U.S. Appl. No. 16/142,545, titled "Armored Graft Material Structure and Method", filed Sep. 26, 2018.
U.S. Appl. No. 16/144,078, titled "Biodegradable Composite Yarn Structure and Method", filed Sep. 27, 2018.
U.S. Appl. No. 16/143,125, titled "Framed Biodegradable Yarn Structure and Method", filed Sep. 26, 2018.
U.S. Appl. No. 16/156,271, titled "Variable Permeability Layered Structure and Method", filed Oct. 10, 2018.

* cited by examiner

GRAFT MATERIAL HAVING HEATED PUNCTURE STRUCTURE AND METHOD

RELATED APPLICATIONS

This application claims the benefit of U.S. Provisional Application No. 62/591,601, filed on Nov. 28, 2017, entitled "ADVANCED GRAFT MATERIALS FOR ENDOVASCULAR APPLICATIONS" of Borglin et al., which is incorporated herein by reference in its entirety.

FIELD

The present application is generally related to an intravascular device and method.

BACKGROUND

A conventional stent-graft typically includes a radially expandable reinforcement structure, formed from a plurality of annular stent rings, and a cylindrically shaped layer of graft material defining a lumen to which the stent rings are coupled. Stent-grafts are well known for use in tubular shaped human vessels.

To illustrate, endovascular aneurysmal exclusion is a method of using a stent-graft to exclude pressurized fluid flow from the interior of an aneurysm, thereby reducing the risk of rupture of the aneurysm and the associated invasive surgical intervention.

The graft material of traditional stent-grafts is extremely hydrophobic and presents a hostile environment for the recruitment and proliferation of cells. The inability of tissue to integrate into the graft material prevents the biological fixation of the stent-graft in vessels and makes the stent-graft susceptible to endoleaks and migration.

SUMMARY

A needle lattice is used to form openings within a graft material to selectively enhance permeability of a prosthesis for tissue integration therein. The needle lattice may be disposed on, for example, a surface of a roller or press. The needle lattice precisely places openings in any pattern and location, and on any textile that forms the graft material. The needle lattice can be heated to fuse the surrounding material of the openings of the textile to prevent movement of the textile and to prevent collapse of the openings. All parameters of the openings, including varying density, patterns, and size of each opening, can be controlled, allowing for the opportunity to selectively enhance and optimize the permeability of the graft material in a vessel. The needle lattice can quickly form multiple openings within a graft material, allowing for quick manufacturing of the prosthesis.

In one aspect, the present disclosure provides a prosthesis includes a graft material including an inner surface and an outer surface, and a plurality of needle-created openings extending through the graft material between the inner surface and the outer surface, each needle-created opening being surrounded by a fused region of the graft material.

In another aspect, the disclosure provides a method includes fabricating a prosthesis including providing a graft material, and forming a plurality of openings within a permeable region of the graft material with a needled lattice that is heated.

In yet another aspect, the disclosure provides an assembly includes a needle lattice including needles disposed over a surface, a heater coupled to the needle lattice, and a graft material that can be penetrated by the needle lattice.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
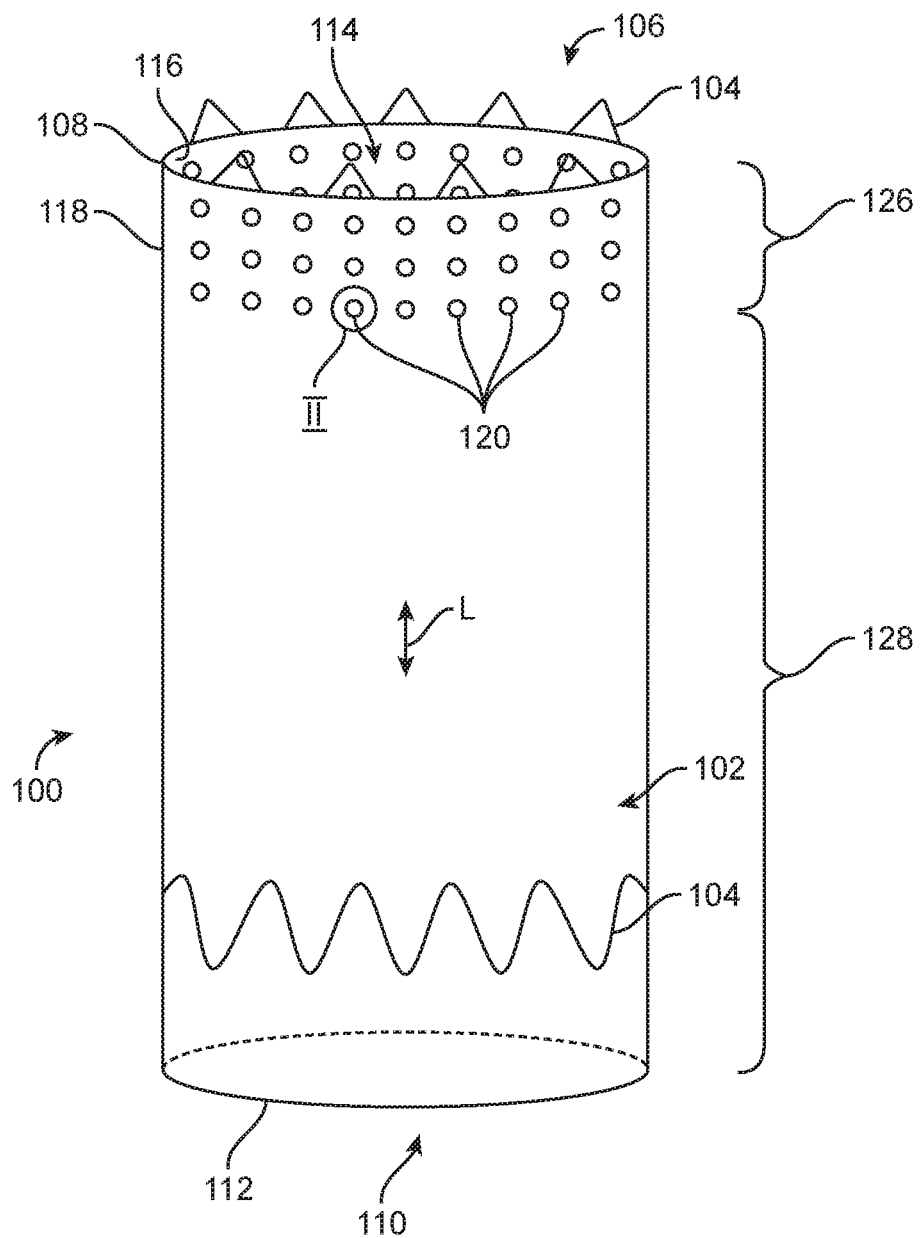
FIG. 1 is a perspective view of a selectively enhanced permeability stent-graft in accordance with one embodiment.

FIG. 1 is a perspective view of a selectively enhanced permeability stent-graft 100, e.g., an abdominal aortic stent-graft, in accordance with one embodiment. Referring now to FIG. 1, stent-graft 100, sometimes called a prosthesis, includes a selectively enhanced permeability graft material 102 and one or more stent rings 104. Illustratively, stent rings 104 are self-expanding stent rings, e.g., nickel titanium alloy (NiTi), sometimes called Nitinol, or a self-expanding member. The inclusion of stent rings 104 is optional and in one embodiment stent rings 104 are not included. In another embodiment, stent rings 104 are balloon expandable stents.

In accordance with this embodiment, graft material 102, sometimes called a textile, includes a proximal opening 106 at a proximal end 108 of graft material 102 and a distal opening 110 at a distal end 112 of graft material 102.

Further, stent-graft 100 includes a longitudinal axis L. A lumen 114 is defined by graft material 102, and generally by stent-graft 100. Lumen 114 extends generally parallel to longitudinal axis L and between proximal opening 106 and distal opening 110 of stent-graft 100.

As used herein, the proximal end of a prosthesis such as stent-graft 100 is the end closest to the heart via the path of blood flow whereas the distal end is the end furthest away from the heart during deployment. In contrast and of note, the distal end of the catheter is usually identified to the end that is farthest from the operator/handle while the proximal end of the catheter is the end nearest the operator/handle.

For purposes of clarity of discussion, as used herein, the distal end of the catheter is the end that is farthest from the operator (the end furthest from the handle) while the distal end of stent-graft 100 is the end nearest the operator (the end nearest the handle), i.e., the distal end of the catheter and the proximal end of stent-graft 100 are the ends furthest from the handle while the proximal end of the catheter and the distal end of stent-graft 100 are the ends nearest the handle. However, those of skill in the art will understand that depending upon the access location, stent-graft 100 and the delivery system descriptions may be consistent or opposite in actual usage.

Graft material 102 is cylindrical having a substantially uniform diameter. However, in other embodiments, graft material 102 varies in diameter and is bifurcated at distal end 112 or is multi-limbed for branching applications. Graft material 102 includes an inner surface 116 and an opposite outer surface 118, e.g., cylindrical surfaces.

In one embodiment, graft material 102 is hydrophobic, e.g., is polyester terephthalate (PET), expanded polyester terephthalate (ePET), or other graft material or textile. As graft material 102 is hydrophobic, graft material 102 in itself presents a hostile environment for the recruitment and the proliferation of cells. However, in accordance with this embodiment, the permeability of graft material 102 is selectively enhance to encourage tissue integration therein.

Figure 2:
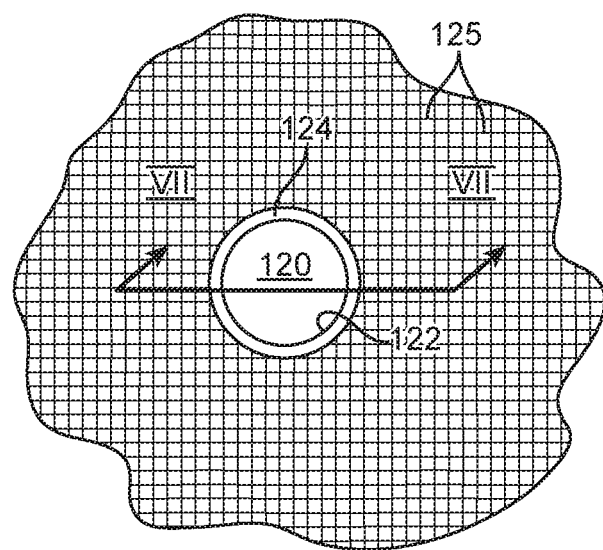
FIG. 2 is an enlarged plan view of a region II of a graft material of the stent-graft of FIG. 1 in accordance with one embodiment.

FIG. 2 is an enlarged plan view of a region II of graft material 102 of stent-graft 100 of FIG. 1 in accordance with one embodiment. Referring now to FIGS. 1 and 2 together, a plurality of openings 120 are formed within graft material 102, an opening 120 being illustrated in FIG. 2. Openings 120 extends entirely through graft material 102 and between inner surface 116 and outer surface 118.

In accordance with this embodiment, openings 120 are circular and include a circumference 122, e.g., an edge of graft material 102 that defines openings 120.

Extending outward from circumference 122 is a fused region 124. Fused region 124 is an area of graft material 102 that has been fused together. For example, openings 120 are formed by a needle lattice, where needles of the needle lattice are heated before and/or after they separate filaments 125 of graft material 102. Openings 120 are sometimes called needle-created openings 120. During formation of openings 120, the heated needles melt fused region 124, which then cools to form a solid fused region 124. In other words, fused region 124 is a region which has been melted and fused together.

In accordance with this embodiment, fused region 124 is shaped as an annulus around opening 120, i.e., extending outward from circumference 122. However, in other embodiments, openings 120 are noncircular shapes, e.g., are linear, oval, conical, or other shapes. Generally, fused region 124 is an area, e.g., a continuous strip, extending outward from and surrounding opening 120.

By forming fused region 124, openings 120 produced by a needle have an inherent resistance to textile wear as filaments 125 along the edge, e.g., circumference 122, of each opening 120 are bonded together by the heat of the needle. This produces a stable textile, e.g., graft material 102, with openings 120 that can be supplemented with bioactive material as discussed further below. In one embodiment, graft material 102 is formed of filaments 125 weaved or otherwise combined together.

Figure 3:
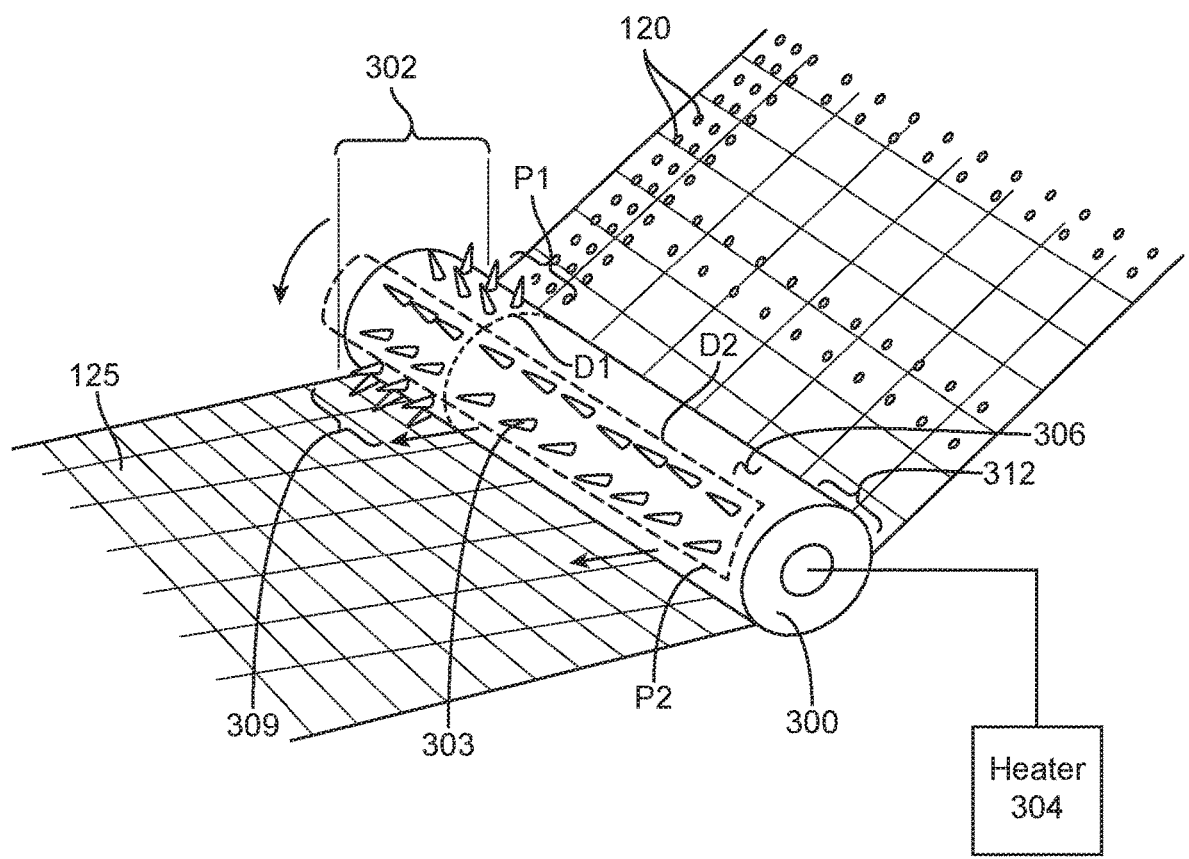
FIG. 3 is a perspective view of a formation of openings using a needle lattice in accordance with one embodiment.
Figure 4:
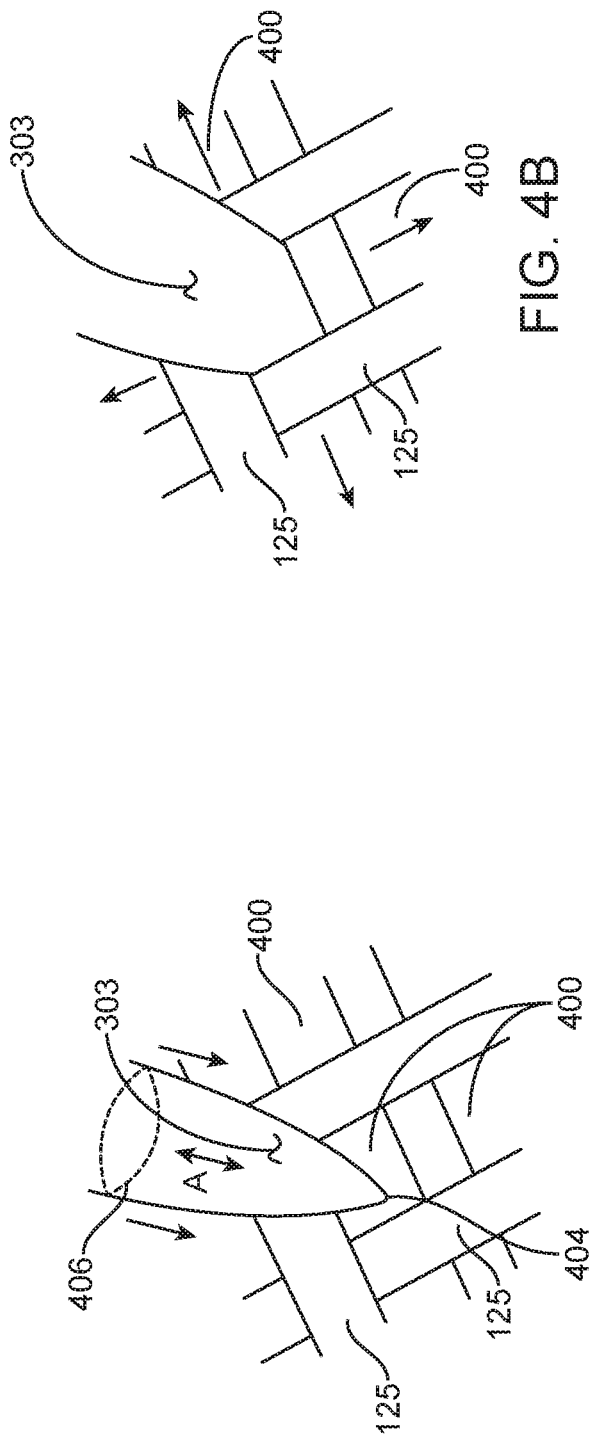
FIG. 4A is an enlarged perspective view of a beginning of insertion of a needle into a space between filaments in accordance with one embodiment.
FIG. 4B is an enlarged perspective view of an insertion of the needle into the space between filaments depicted in FIG. 4A in accordance with one embodiment.
FIG. 4C is an enlarged perspective view of the same location as FIG. 4B after an opening has been formed and the needle has been removed in accordance with one embodiment.

FIG. 3 is a perspective view of a formation of openings 120 using a needle lattice 302 in accordance with one embodiment. FIG. 4A is an enlarged perspective view of a beginning of insertion of a needle 303 into a space 400 between filaments 125 in accordance with one embodiment. FIG. 4B is an enlarged perspective view of an insertion of needle 303 into space 400 between filaments 125 depicted in FIG. 4A in accordance with one embodiment. FIG. 4C is an enlarged perspective view of the same location as FIG. 4B after opening 120 has been formed and needle 303 has been removed in accordance with one embodiment.

Graft material 102, which is formed of filaments 125, may be a flat sheet at the time of formation of openings 120. After formation of openings 120, the opposite ends of the flat sheet of graft material 102 may be brought together and sewn or otherwise combined together such that graft material 102 forms a cylinder as depicted in FIG. 1.

Referring now to FIGS. 3, 4A-4C together, a roller 300 which includes needle lattice 302 is rolled over filaments 125 that are woven or otherwise combined together. Needle lattice 302 includes needles 303 positioned on a surface 306, and in FIG. 3 needle lattice 302 may include needles 303 in a pattern P1 and a pattern P2. Each of needles 303 may be oriented to be pointing away from surface 306. That is, a tip 404 of needle 303 is also the farthest point of needle 303 from surface 306. Needles 303 may be spaced uniformly across surface 306 such that the distance between any pair of neighboring needles 303 is constant across surface 306. Alternatively, needles 303 may form non-uniform patterns on surface 306 such that the distances between pairs of neighboring needles 303 varies across surface 306. Surface 306 upon which needles 303 are positioned is a cylindrical surface in accordance with this embodiment, but may have other shapes in other embodiments.

Each of needles 303 are long enough to fully pierce graft material 102, i.e., long enough to be fully inserted through spaces 400. Each of needles 303 are short enough to resist deflection, i.e., short enough not to be bent before or after insertion into spaces 400. In this embodiment, cross-sectional areas of needle 303, when looking down a first axis A of needle 303 that is oriented with the shortest distance of the sharp point of needle 303 to a base 406 of needle 303, are circular. However, in other embodiments, cross-sectional areas of needle 303 may be noncircular shapes, e.g., are linear, oval, conical, or other shapes.

Needle 303 may be a three-dimensional shape with base 406 having a larger cross-sectional area than tip 404, where moving along from base 406 to tip 404, the cross-sectional areas grow successively smaller until the shape of needle 303 tapers into a point at tip 404. Alternatively, needle 303 may be a shape that tapers from a large cross-sectional area into a smaller cross-sectional area with a finite area rather than tapering into a point, so that tip 404 of needle 303 is blunt.

For convenience of illustration, FIG. 3 depicts at least two embodiments of needle lattice 302, where each embodiment has a different pattern of needles 303 disposed on surface 306 of roller 300. For the purposes of this discussion, a top 309 of roller 300 refers to the upper left of roller 300 as depicted in FIG. 3. One embodiment includes the pattern P1 including needles 303 positioned only above a dashed line D1, i.e. roller 300 includes only needles 303 at top 309 of roller 300 encircling roller 300. Another embodiment includes the pattern P2 including only needles 303 that are bounded by dashed lines D2, so that a strip of needles 303 runs longitudinally from top 309 of roller 300 to a bottom 312 of roller 300, and the other regions of surface 306 do not include needles 303.

For convenience of illustration, FIG. 3 depicts openings 120 formed in filaments 125 by both pattern P1 and pattern P2 when roller 300 is rolled over filaments 125 in the direction depicted by the arrows. However, roller 300 with pattern P1 would naturally only form openings 120 on the top edge of the sheet, while roller 300 with pattern P2 would naturally only form openings 120 in strips of openings 120 corresponding to the longitudinal strips of needles 303, without any openings 120 formed between such strips of openings 120.

In light of this disclosure, those of skill in the art would understand that any number of other patterns of needle lattice 302 are possible. In one embodiment, needle lattice 302 may cover the entire surface 306 of roller 300. In other embodiments, needle lattice 302 may cover certain areas of roller 300 different or in addition to those areas depicted in FIG. 3 as discussed below.

Because filaments 125 are woven or otherwise combined together, there are spaces 400 between filaments 125. As roller 300 is rolled over the sheet of filaments 125, each needle 303 of needle lattice 302 is inserted through space 400, as shown in FIG. 4B. In one embodiment, a cross-sectional area of needle 303 is larger than an area of space 400 between filaments 125, such that the insertion of needle 303 into space 400 results in filaments 125 being pushed aside to accommodate the cross-sectional area of needle 303. However, in other embodiments, the cross-sectional area of needle 303 may be equal to or less than the area of space 400 between filaments 125.

Needle 303 may be heated before, during, and/or after insertion into space 400. Needle 303 may be heated by a heater 304 depicted in FIG. 3. In one embodiment, needle lattice 302 is heated so that needle lattice 302 is at a constant heat as roller 300 rolls along filaments 125. Once needle 303 is inserted into space 400, as shown in FIG. 4B, the heat of needle 303 reflows filaments 125 around needle 303 into reflowed filaments 402. In an embodiment depicted by FIG. 4B, when needle 303 is inserted into space 400, it may push apart filaments 125 by its cross-sectional area, which may be larger than the area of space 400 within which needle 303 inserted. In another embodiment, needle 303 may be brought proximal to space 400 but not contacting the surrounding filaments 125 nor penetrating space 400, when the heat of needle 303 due to the proximity of needle 303 to filaments 125 is sufficient to form fused region 124.

In yet another embodiment, graft material 102 does not comprise filaments 125, but instead includes a continuous sheet of material without spaces 400. Needles 303 pierce graft material 102 and form their own holes in graft material 102. Needles 303 then form fused regions 124 around the holes by the heat of needles 303.

In the embodiment depicted in FIG. 4B, reflowed filaments 402 are filaments 125 that have been subjected to heat from needle 303 such that filaments 125 have reflowed to form openings 120 where spaces 400 once were, formed fused regions 124 around openings 120, and become reflowed filaments 402. Reflowed filaments 402 may still be separate, i.e., not fused but still woven together, outside of fused regions 124. In this embodiment, FIG. 4C depicts spaces 400 remaining within reflowed filaments 402 after formation of opening 120. Spaces 400 could have the same area as before reflowing, or spaces 400 could be smaller or larger after the reflowing. However, in other embodiments, reflowed filaments 402 could include only openings 120 which have been formed by needle lattice 302, without including any spaces 400 after insertion and removal of needle lattice 302.

Once openings 120 are formed, the reflowed filaments 402 are prevented from shifting around openings 120 and collapsing openings 120, since openings 120 have been fused by the heating of needles 303 such that they have fused regions 124 surrounding them.

Figure 5:
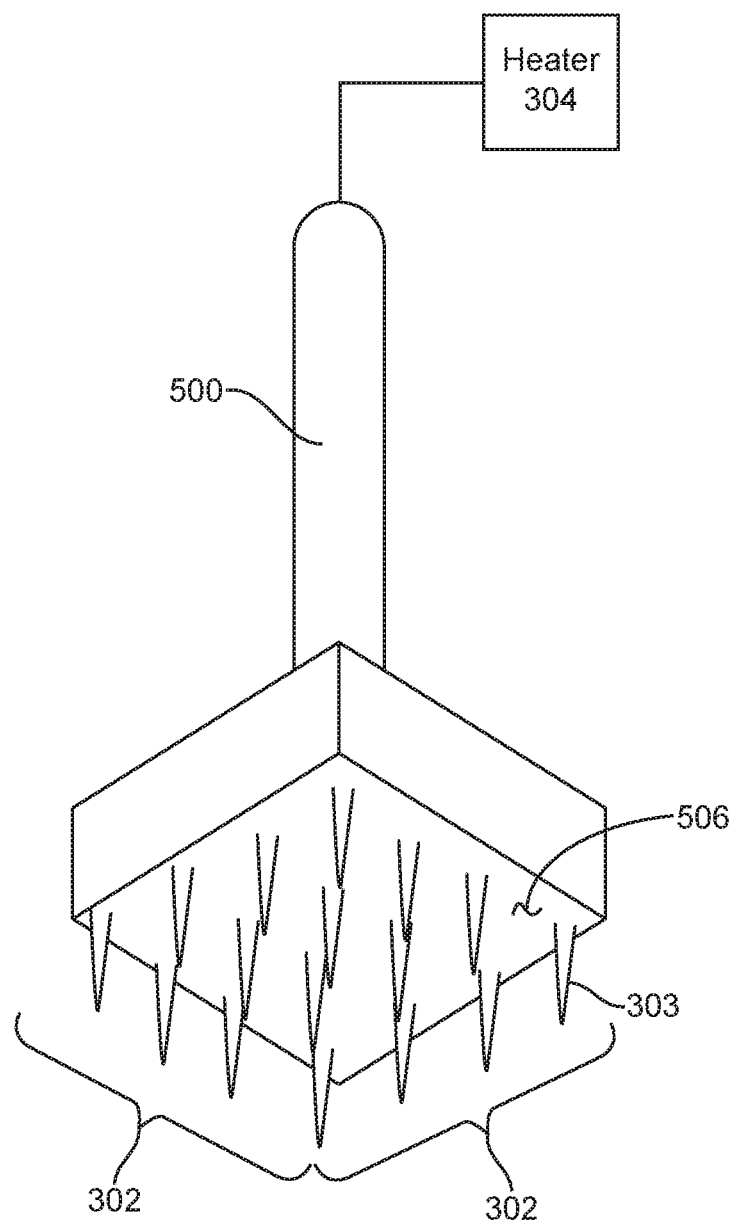
FIG. 5 is a perspective view of a press with a needle lattice in accordance with one embodiment.

FIG. 5 is a perspective view of another embodiment that includes a press 500 with needle lattice 302 on a surface 506 of press 500. In accordance with this embodiment, surface 506 is a flat plane. As with the embodiments of roller 300 described above, needle lattice 302 positioned on press 500 may, in one embodiment, be uniformly distributed over the entire surface 506 of press 500. In other embodiments, needle lattice 302 may be more densely distributed towards one end of surface 506 of press 500, may not be distributed on one end of surface 506, and/or may have other patterns such as alternating strips of needles between strips where no needles are present, and so forth.

Figure 6:
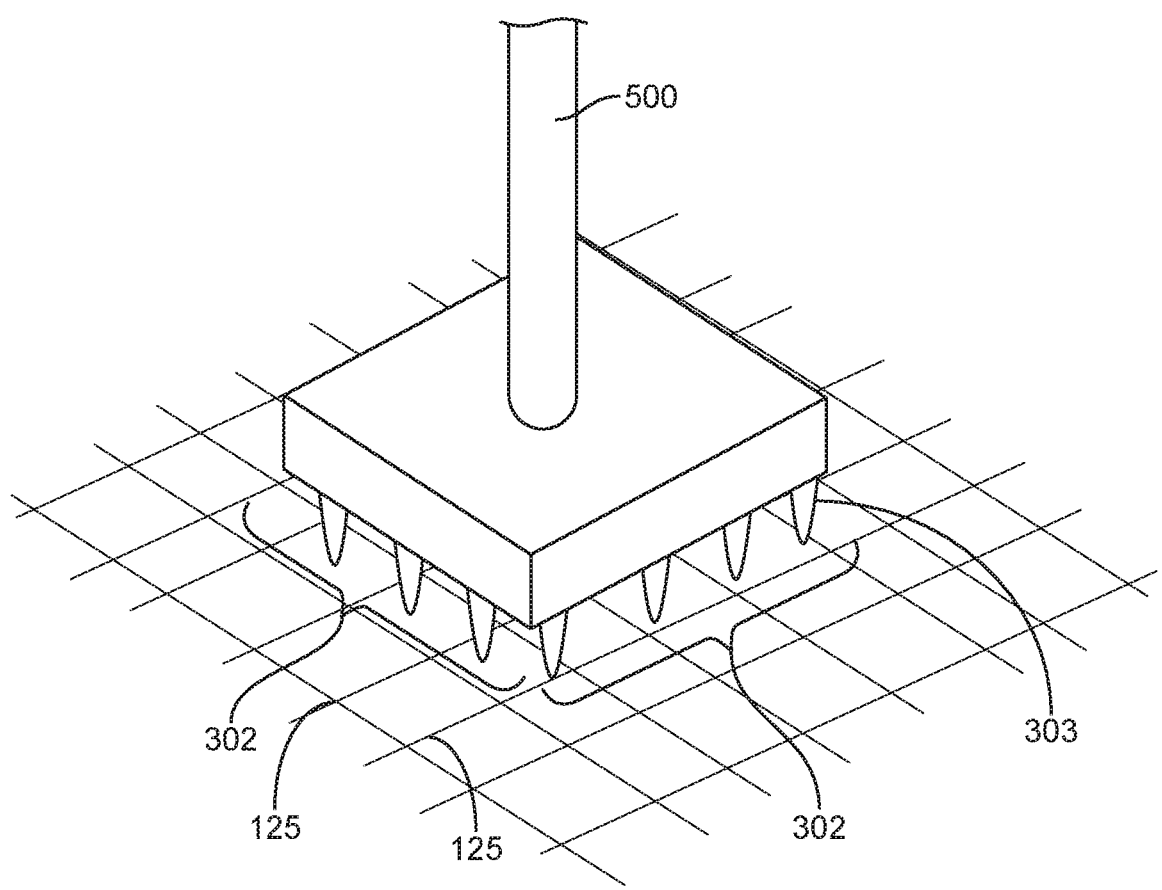
FIG. 6 is a perspective view of the press with the needle lattice of FIG. 5 applied to a graft material in accordance with one embodiment.

FIG. 6 is a perspective view of press 500 being pressed into filaments 125. The process of the insertion of needles 303 follows that depicted in FIGS. 4A, 4B, and 4C. As with roller 300, needle 303 may be heated before, after, and/or during insertion of needle 303 between filaments 125. In one embodiment, press 500 is pressed into filaments 125, needle lattice 302 is heated to fuse filaments 125 and form openings 120, and press 500 is removed from filaments 125.

In one embodiment, once openings 120 have been introduced into graft material 102 in accordance with any one of the embodiments discussed above, a bioabsorbable material is then used to fill openings 120 in graft material 102 as discussed below.

Figure 7A:
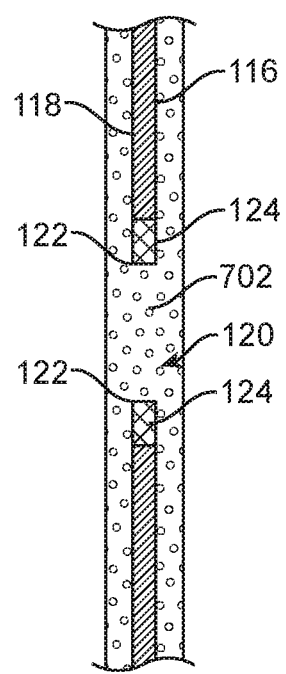
FIG. 7A is a cross-sectional view of an opening along the line VII-VII of FIG. 2 in accordance with one embodiment.

FIG. 7A is a cross-sectional view of opening 120 along the line VII-VII of FIG. 2 in accordance with one embodiment. In accordance with this embodiment, a bioactive material 702 fills openings 120. Bioactive material 702 is applied as a layer to cover outer surface 118, inner surface 116, or both outer surface 118 and inner surface 116 of graft material 102. Bioactive material 702 can be applied to the entire area of graft material 102. However, in another embodiment, bioactive material 702 is applied to selective zones of graft material 102, e.g., to the areas where openings 120 are created only.

Figure 7B:
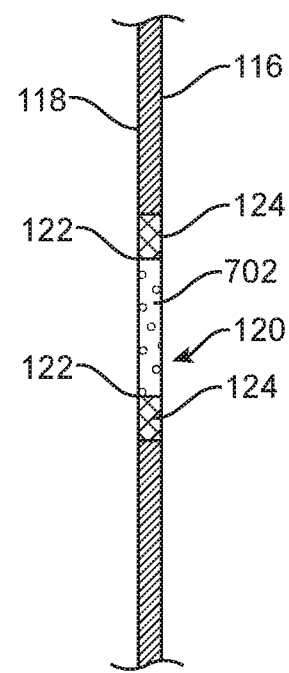
FIG. 7B is a cross-sectional view of the opening along the line VII-VII of FIG. 2 in accordance with another embodiment.

FIG. 7B is a cross-sectional view of opening 120 along the line VII-VII of FIG. 2 in accordance with another embodiment. In accordance with this embodiment, bioactive material 702 fills openings 120. Bioactive material 702 is a plug that fills opening 120 without extending onto outer surface 118 and/or inner surface 116 of graft material 102. In light of this disclosure, those of skill in the art will understand that bioactive material 702 may not be entirely contained within openings 120 and some bioactive material 702 may overlap onto outer surface 118 and/or inner surface 116 of graft material 102 in one embodiment.

Referring now to FIGS. 7A and 7B together, by filling openings 120, bioactive material 702 reinforces the mechanical properties of graft material 102. Bioactive material 702 enables acute resistance to type IV endoleaks, i.e., leaks through graft material 102. Furthermore, in one embodiment, bioactive material 702 degrades on a biological timescale that matches and promotes the speed of tissue in growth. As the tissue grows into openings 120 and replaces bioactive material 702, type IV endoleaks are prevented and migration resistance of stent-graft 100 is improved. Generally, the structure of openings 120 along with bioactive material 702 allows for the recruitment and proliferation of cells and for neovascularization to occur.

Further, in one embodiment, bioactive material 702 is a tissue healing promoting material that serves to promote the healing process, e.g., the recruitment and proliferation of cells that drive the healing process. Examples of bioactive material 702 include polymer polyglycolic-lactic acid (PGLA), and poly(glycerol sebacate) (PGS).

Bioactive material 702 is applied using any one of a number of techniques in accordance with various embodiments. For example, bioactive material 702 is applied by spraying, coating, and/or brushing. In one embodiment, bioactive material 702 is vacuum applied, i.e., a vacuum is formed within graft material 102 which draws (sucks) bioactive material 702 into openings 120. In yet another embodiment, bioactive material 702 is applied by electro spinning, i.e., using electric force to draw bioactive material 702 into openings 120. Although a few examples are provided, bioactive material 702 can be applied in a variety of different techniques in accordance with different embodiments.

Referring again to FIG. 1, in accordance with one embodiment, openings 120 are formed within graft material 102 at or adjacent to proximal end 108 of graft material 102. The region 126 of graft material 102 in which openings 120 are formed is referred to as a permeable zone 126 of graft material 102. The region 128 of graft material 102, which has an absence of openings 120, sometimes called native graft material 102, is referred to as a non-permeable zone 128 of graft material 102. Permeable zone 126 extends distally from proximal end 108 to non-permeable zone 128. Non-permeable zone 128 extends distally from permeable zone 126 to distal end 112.

Figure 8:
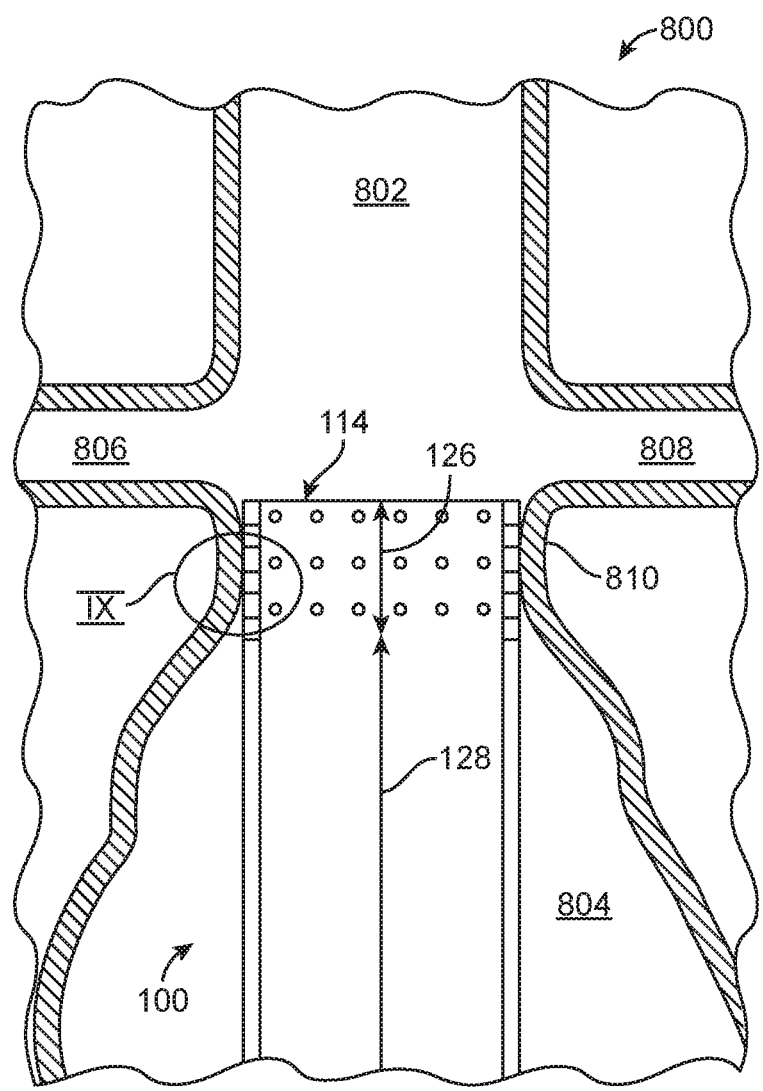
FIG. 8 is a cross-sectional view of a vessel assembly including the stent-graft of FIGS. 1 and 2 in accordance with one embodiment.

FIG. 8 is a cross-sectional view of a vessel assembly 800 including stent-graft 100 of FIGS. 1 and 2 in accordance with one embodiment. Referring now to FIG. 8, a vessel 802, e.g., the aorta, includes an aneurysm 804. Stent-graft 100 is deployed into vessel 802 to exclude aneurysm 804 using any one of a number of techniques well known to those of skill in the art.

Emanating from vessel 802 is a first branch vessel 806 and a second branch vessel 808, sometimes called visceral branches of the abdominal aorta. The location of branch vessels 806, 808 vary from patient to patient. Examples of branch vessels include the renal arteries (RA) and the superior mesenteric artery (SMA).

Stent-graft 100 is deployed just distal of branch vessels 806, 808. Permeable zone 126 is deployed in the landing zone 810 between branch vessels 806, 808 and aneurysm 804. Over time, tissue from vessel 802 will become integrated with openings 120 and more generally within graft material 102, thus preventing leakage around permeable zone 126 and migration of stent-graft 100 as described below in reference to FIGS. 9 and 10.

Figure 9:
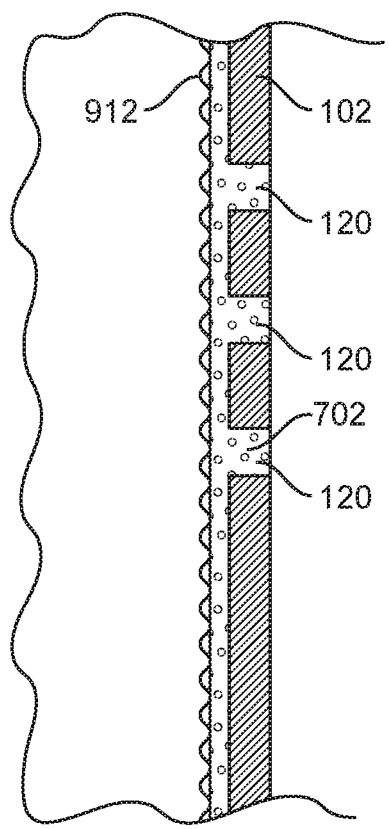
FIG. 9 is an enlarged cross-sectional view of a region IX of FIG. 8 just after initial deployment of the stent-graft in accordance with one embodiment.
Figure 10:
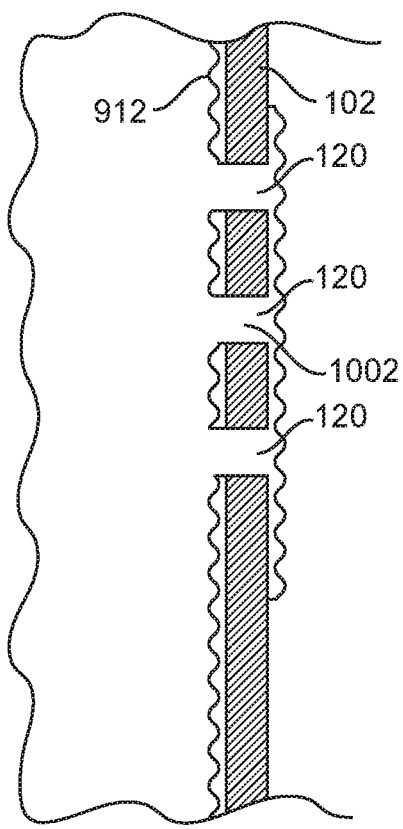
FIG. 10 is an enlarged cross-sectional view of the region IX of FIG. 8 after a period of time after deployment of the stent-graft in accordance with one embodiment.

FIG. 9 is an enlarged cross-sectional view of a region IX of FIG. 8 just after initial deployment of stent-graft 100 in accordance with one embodiment. FIG. 10 is an enlarged cross-sectional view of the region IX of FIG. 8 after a period of time after deployment of stent-graft 100 in accordance with one embodiment.

Referring to FIG. 9, upon deployment of stent-graft 100, permeable zone 126 is in contact with a vessel wall 912 of vessel 802. Bioactive material 702 seals openings 120 in accordance with this embodiment. Over time, bioactive material 702 is replaced with tissue 1002 from vessel wall 912 that integrates within and through openings 120 as illustrated in FIG. 10. Tissue 1002 prevents leakage around permeable zone 126 and migration of stent-graft 100.

Referring again to FIG. 8, once anchored within vessel 802, blood flows through lumen 114 and more generally through stent-graft 100, thus excluding aneurysm 804.

Although a particular example of permeable zone 126 and non-permeable zone 128 are provided, by using needle lattice 302 to form openings 120, the location of permeable zone 126 and non-permeable zone 128 can be readily modified depending upon the particular application desired as discussed further below in accordance with other embodiments.

More particularly, in accordance with this embodiment, a method to enhance tissue integration through porosity while providing resistance to endoleaks and maintaining sufficient mechanical strength of graft material 102 is provided. This is accomplished by selectively generating precise openings 120, sometimes called ingress channels, using a needle lattice and subsequently filling openings 120 with bioabsorbable material 702.

Some examples in accordance with various embodiments are provided below.

Figure 11:
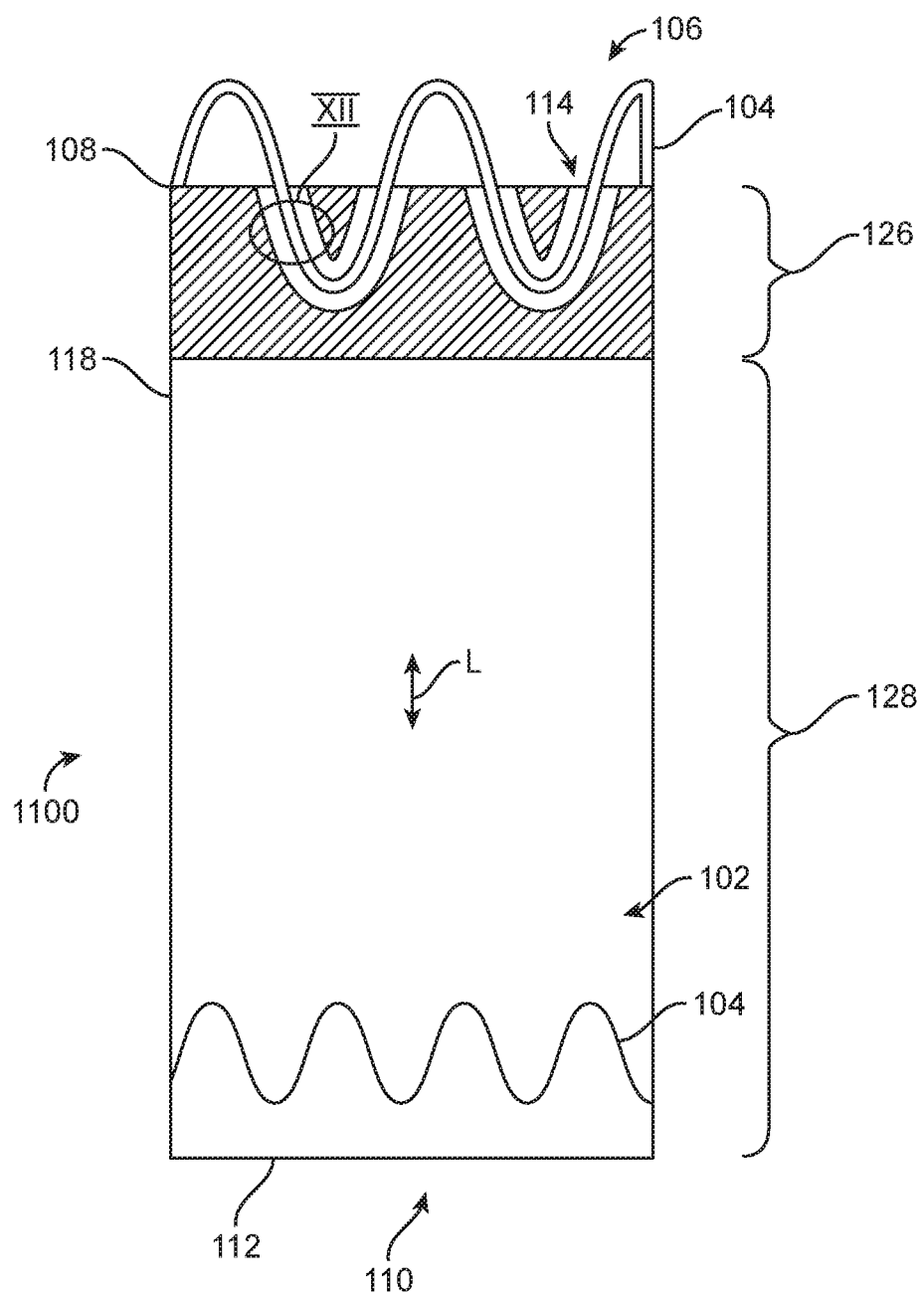
FIG. 11 is a perspective view of an enhanced permeability stent-graft in accordance with another embodiment.

FIG. 11 is a perspective view of an enhanced permeability stent-graft 1100 in accordance with another embodiment. FIG. 12A is an enlarged perspective view of a region XII of stent-graft 1100 of FIG. 11 in accordance with one embodiment. Stent-graft 1100 of FIG. 11 is similar to stent-graft 100 of FIG. 1 and only the significant differences are discussed below.

Referring now to FIG. 11, permeable zone 126, which includes openings 120, is indicated as a shaded region. As shown in FIG. 12A, permeable zone 126 surrounds but does not overlap with stent ring 104 or sutures 1202 that attach stent ring 104 to graft material 102. In other words, non-permeable zone 128, i.e., graft material 102 without openings 120, overlaps stent ring 104 and sutures 1202.

By forming non-permeable zone 128 to overlap stent ring 104 and sutures 1202, the region of graft material 102 acting in cooperation with stent ring 104 and sutures 1202 has maximized strength, e.g., the strength of graft material 102. This minimizes the possibility of failure of graft material 102 due to the stress placed upon graft material 102 from stent ring 104 and sutures 1202.

Figure 12B:
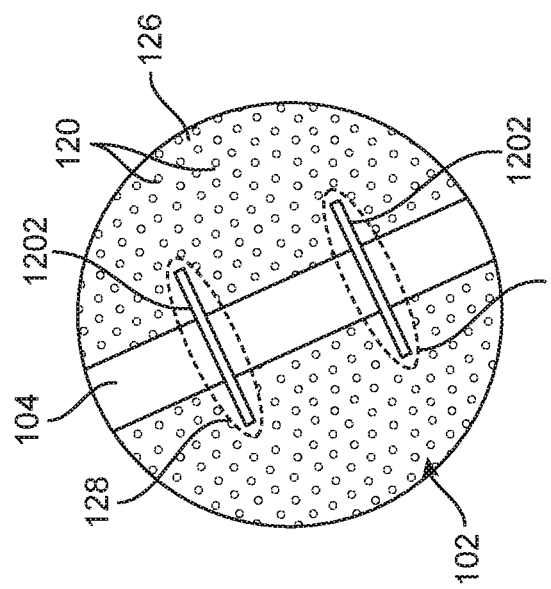
FIG. 12B is an enlarged perspective view of the region XII of the stent-graft of FIG. 11 in accordance with another embodiment.
Figure 12A:
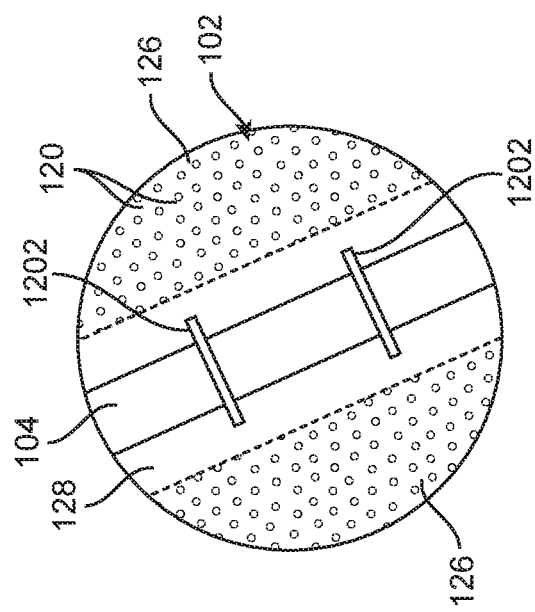
FIG. 12A is an enlarged perspective view of a region XII of the stent-graft of FIG. 11 in accordance with one embodiment.

FIG. 12B is an enlarged perspective view of region XII of stent-graft 1100 of FIG. 11 in accordance with another embodiment. As shown in FIG. 12B, permeable zone 126 overlaps with stent ring 104 but does not overlap with sutures 1202. In other words, non-permeable zone 128, i.e., graft material 102 without openings 120, overlaps sutures 1202. By forming non-permeable zone 128 to overlap sutures 1202 are stitched into regions of graft material 102 with maximized strength. This minimizes the possibility of failure of graft material 102 due to the stress placed upon graft material 102 from sutures 1202.

Figure 13:
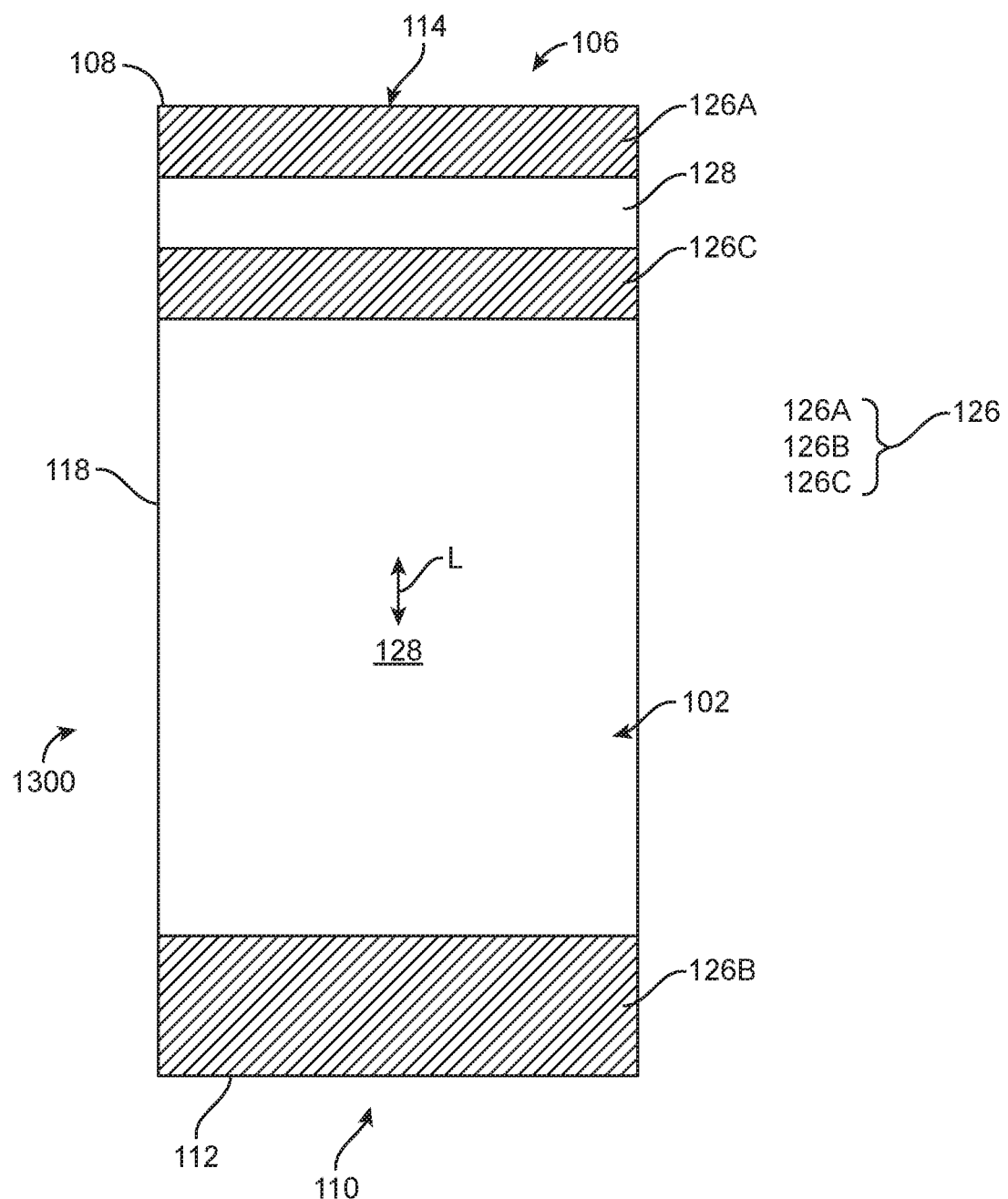
FIG. 13 is a perspective view of an enhanced permeability stent-graft in accordance with another embodiment.

FIG. 13 is a perspective view of an enhanced permeability stent-graft 1300 in accordance with another embodiment. Stent-graft 1300 of FIG. 13 is similar to stent-graft 100 of FIG. 1 and only the significant differences are discussed below. In FIG. 13, stent rings 104 as illustrated in FIG. 1 are not illustrated for simplicity although stent-graft 1300 includes stent rings 104 in other embodiments.

Referring now to FIG. 13, permeable zone 126 is formed as one or more discrete circumferential bands (regions or rings) around graft material 102. In accordance with this embodiment, permeable zone 126 includes three discrete circumferential permeable zones 126A, 126B, 126C. For example, a proximal permeable zone 126A is formed at proximal end 108 and a distal permeable zone 126B is formed at distal end 112 of graft material 102. Illustratively, proximal permeable zone 126A and a distal permeable zone 126B enhance tissue integration at both proximal and distal ends 108, 112 of graft material 102.

In accordance with this embodiment, a middle permeable zone 126C is formed separated from but between bands 126A, 126B. Non-permeable zones 128, which are also shaped as circumferential bands, are located between and separate permeable zones 126A, 126B, 126C to maintain the strength of stent-graft 1300. Although a particular arrangement of permeable zones 126A, 126B, 126C is illustrated and discussed, generally, one or more circumferential permeable zones are formed.

Permeable zones 126A, 126B, 126C may be formed by a roller 300. In accordance with this embodiment, needle lattice 302 may encircle both top 309 of roller 300 with two strips of needles 303 and bottom 312 of roller 300 with one larger strip of needles 303, such that when roller 300 is rolled over filaments 125, needle lattice 302 forms openings 120 in the three discrete circumferential permeable zones 126A, 126B, and 126C.

Figure 14:
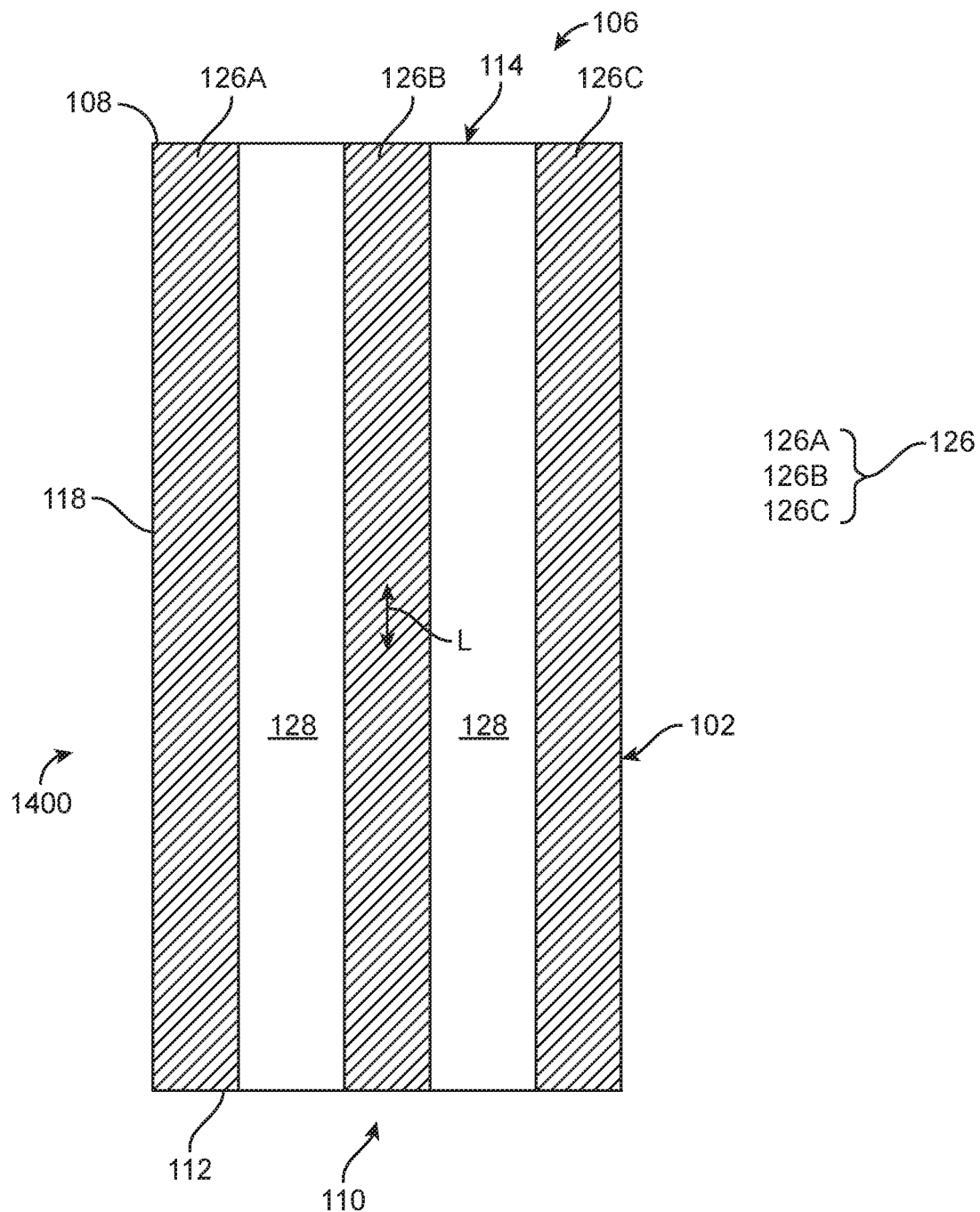
FIG. 14 is a perspective view of an enhanced permeability stent-graft in accordance with yet another embodiment.

FIG. 14 is a perspective view of an enhanced permeability stent-graft 1400 in accordance with yet another embodiment. Stent-graft 1400 of FIG. 14 is similar to stent-graft 100 of FIG. 1 and only the significant differences are discussed below. In FIG. 14, stent rings 104 as illustrated in FIG. 1 are not illustrated for simplicity although stent-graft 1400 includes stent rings 104 in other embodiments.

Referring now to FIG. 14, permeable zone 126 is formed as one or more discrete longitudinal strips (regions) extending along the length of graft material 102 generally parallel to longitudinal axis L. For example, permeable zone 126 includes a plurality of discrete longitudinal permeable zones 126A, 126B, 126C although there may be additional longitudinal permeable zones not visible in the view of FIG. 14, e.g., on the backside of stent-graft 1400. For example, each permeable zone 126A, 126B, 126C is formed extending the entire length from proximal end 108 to distal end 112 of graft material 102. Illustratively, permeable zones 126A, 126B, 126C enhance tissue integration along the entire length of graft material 102.

Non-permeable zones 128, which are also shaped as longitudinal strips, are located between and separate permeable zones 126A, 126B, 126C to maintain the strength of stent-graft 1400. Although a particular arrangement of permeable zones 126A, 126B, 126C is illustrated and discussed, generally, one or more longitudinal permeable zones 126A, 126B, 126C are formed. Further, the length of permeable zones 126A, 126B, 126C vary in other embodiments, e.g., do not extend the entire length of stent-graft 1400.

Permeable zones 126A, 126B, 126C may be formed by a roller 300. In accordance with this embodiment, needle lattice 302 may encircle roller 300 by alternating between longitudinal strips of needles 303 and longitudinal strips where no needles 303 are present, such that when roller 300 is rolled over filaments 125, openings 120 are formed in the three discrete longitudinal permeable zones 126A, 126B, and 126C.

Figure 15:
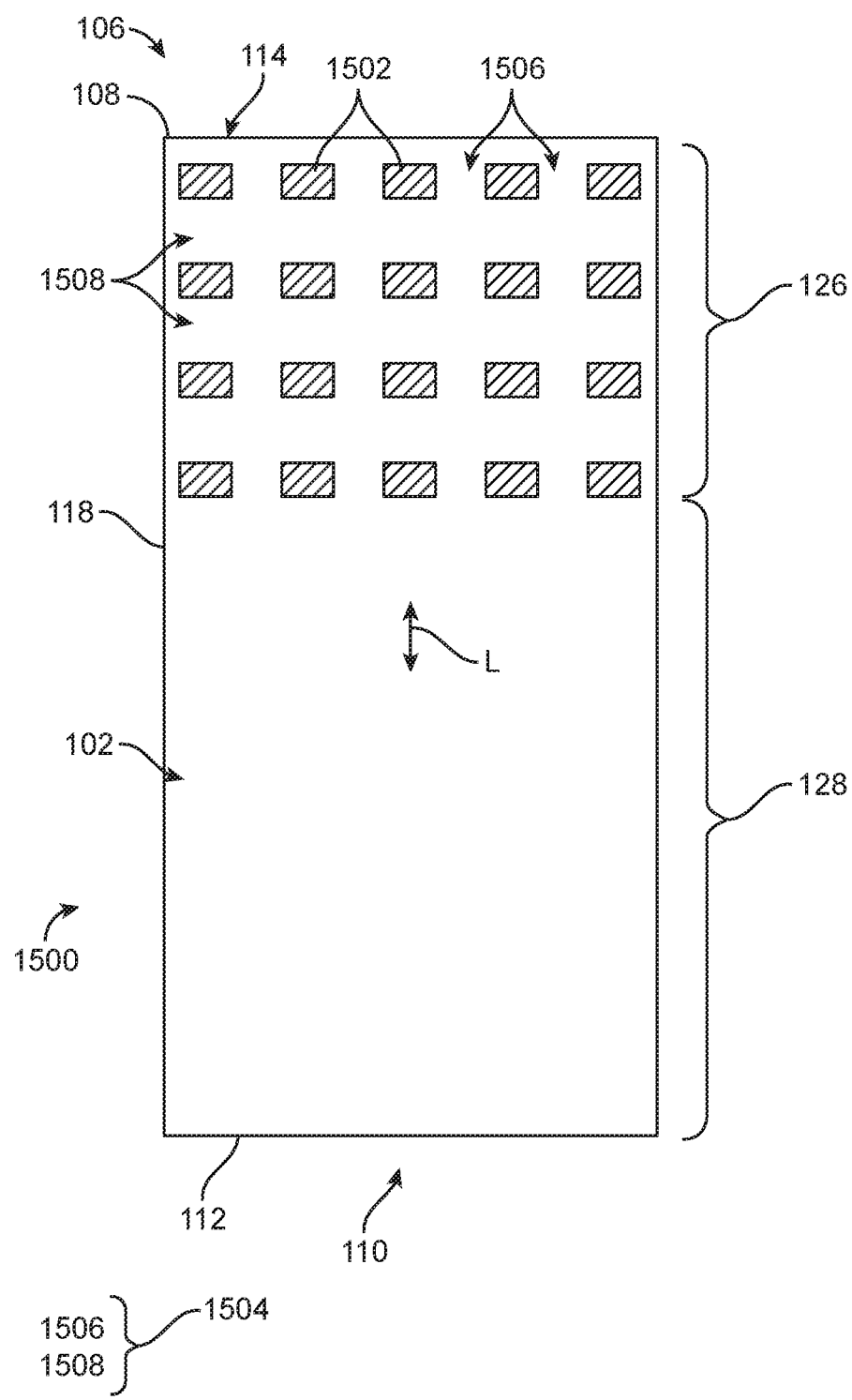
FIG. 15 is a perspective view of an enhanced permeability stent-graft in accordance with yet another embodiment.

FIG. 15 is a perspective view of an enhanced permeability stent-graft 1500 in accordance with yet another embodiment. Stent-graft 1500 of FIG. 15 is similar to stent-graft 100 of FIG. 1 and only the significant differences are discussed below. In FIG. 15, stent rings 104 as illustrated in FIG. 1 are not illustrated for simplicity although stent-graft 1500 includes stent rings 104 in other embodiments.

Referring now to FIG. 15, permeable zone 126 is formed as one or more discrete areas (regions). For example, permeable zone 126 includes a plurality of discrete permeable zones 1502 adjacent proximal end 108. For example, each permeable zone 1502 is formed as a rectangle.

Permeable zones 1502 are arranged in columns, e.g., longitudinally and in rows, e.g., circumferentially. Illustratively, permeable zones 1502 define a non-permeable array 1504, e.g., in a checkerboard shape. Non-permeable array 1504 includes non-permeable longitudinal strips 1506 intersecting non-permeable circumferential bands 1508.

Non-permeable array 1504 is between and separates permeable zones 1502 to maintain the strength of stent-graft 1500 while permeable zones 1502 enhances tissue integrations. Although a particular arrangement of permeable zones 1502 is illustrated and discussed, permeable zones 1502 are formed in different arrangements in different embodiments. For example, diagonal uncut regions are created in another embodiment. In yet another embodiment, a cut pattern which has circumferential, longitudinal and/or diagonal lines are created, e.g., which match the original textile mechanical properties while still providing regions for tissue ingrowth.

Figure 16:
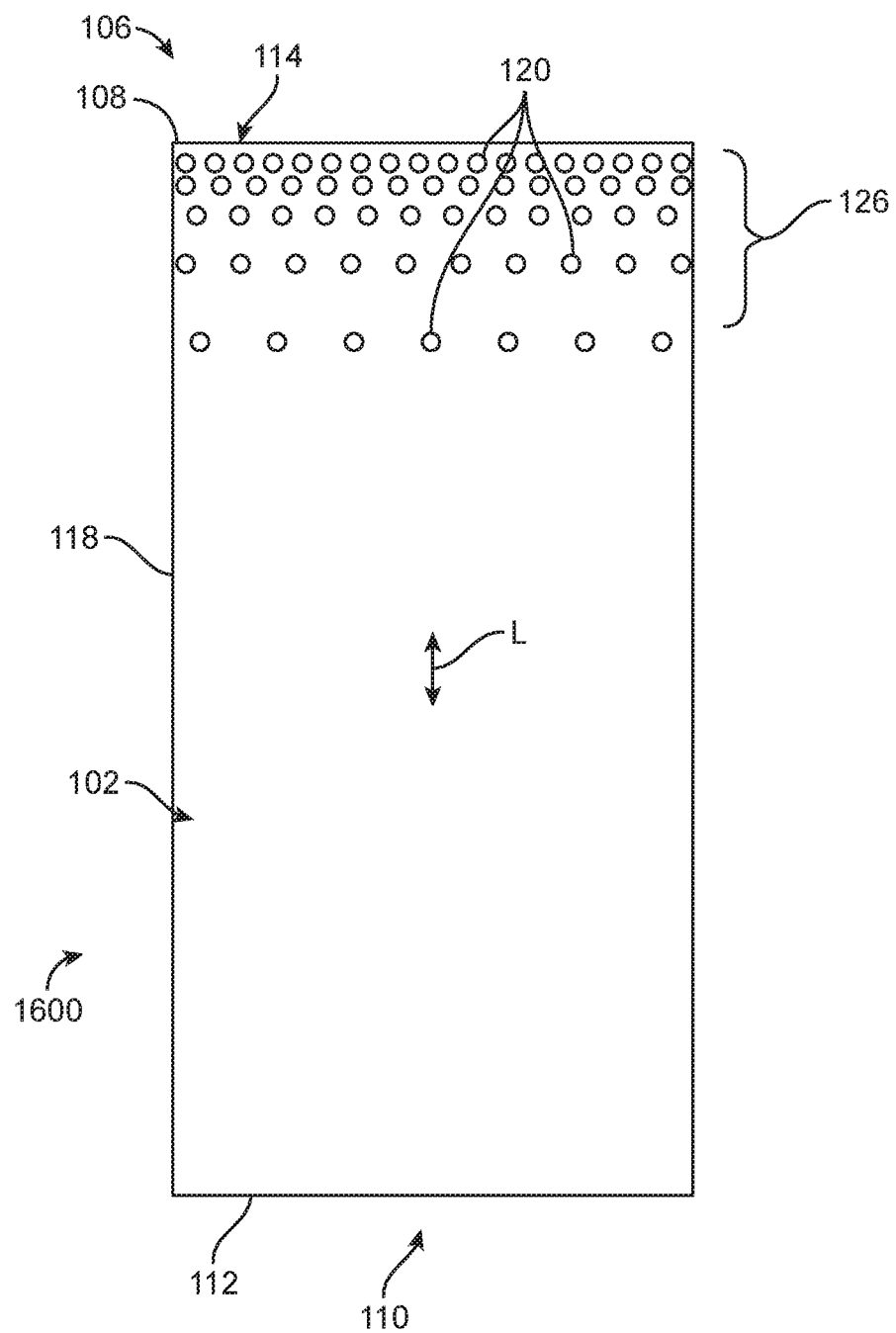
FIG. 16 is a perspective view of an enhanced permeability stent-graft in accordance with yet another embodiment.

FIG. 16 is a perspective view of an enhanced permeability stent-graft 1600 in accordance with yet another embodiment. Stent-graft 1600 of FIG. 16 is similar to stent-graft 100 of FIG. 1 and only the significant differences are discussed below. In FIG. 16, stent rings 104 as illustrated in FIG. 1 are not illustrated for simplicity although stent-graft 1600 includes stent rings 104 in other embodiments.

Referring now to FIG. 16, permeable zone 126 is formed with a varying density of openings 120, e.g., a varying number of openings 120 per given area of graft material 102. For example, the density of openings 120 is greatest at proximal end 108 and decreases linearly as the distance from proximal end 108 increases.

Illustratively, the density is greatest at proximal end 108 to maximize tissue integration at proximal end 108. Then as the distance from proximal end 108 increase, less tissue integration occurs while the strength of graft material 102 increases due to the decreasing density of openings 120. For example, the density is greatest in the seal zone, and then the density tapers out towards regions which will be interfacing with the aneurysm sac. Although a particular arrangement of density variation of openings 120 is illustrated and discussed, permeable zone 126 is formed with different density arrangements in different embodiments depending upon the particular application.

Permeable zone 126 may be formed by roller 300. In accordance with this embodiment, spacing of needles 303 within needle lattice 302 may be denser towards top 309 of roller 300, such that when roller 300 is rolled over filaments 125, openings 120 are formed in permeable zone 126 with the density depicted in FIG. 16.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A method comprising:
   fabricating a prosthesis comprising:
   providing a graft material;
   forming a plurality of openings within a permeable region of the graft material with a needle lattice that is heated; and
   filling the openings with a bioactive material; and
   deploying the prosthesis within a vessel, wherein the bioactive material encourages tissue growth through the openings.

2. The method of claim 1 wherein after a period of time after the deploying, tissue from the vessel integrates within and through the openings, the tissue preventing migration of the prosthesis.

3. The method of claim 1 wherein forming the plurality of openings comprises:
   applying the needle lattice onto the graft material so that needles of the needle lattice are inserted into spaces between filaments of the graft material; and
   heating the needle lattice so that the filaments of the graft material surrounding the needles of the needle lattice reflow and form the openings and a fused region surrounding each of the openings.

4. The method of claim 1 wherein forming the plurality of openings comprises:
   applying the needle lattice onto the graft material so that needles of the needle lattice pierce through the graft material; and wherein the graft material is a continuous sheet.

5. The method of claim 3 wherein a roller comprises a cylindrical surface, the needles of the needle lattice are disposed on the cylindrical surface, and applying the needle lattice comprises rolling the roller over the graft material.

6. The method of claim 3 wherein a press comprises a flat surface, the needles of the needle lattice are disposed on the flat surface, and applying the needle lattice comprises pressing the press onto the graft material.

7. The method of claim 5 wherein the needle lattice comprises a varying density of needles over the cylindrical surface.

8. The method of claim 5 wherein the cylindrical surface comprises a first region and a second region, wherein the needles are disposed only in the first region.

9. The method of claim 3 wherein the needles push apart the filaments surrounding the spaces when they are inserted into the spaces.

\* \* \* \* \*